United States Patent
Horne et al.

(10) Patent No.: US 9,308,081 B2
(45) Date of Patent: Apr. 12, 2016

(54) APPARATUS AND METHODS FOR NIPPLE FORMATION VIA COLLAPSIBLE DEVICES

(75) Inventors: Kenneth N. Horne, San Francisco, CA (US); Sergio Salinas, Redwood City, CA (US); Geoffrey C. Gurtner, Stanford, CA (US); Michael H. Rosenthal, Menlo Park, CA (US); Christopher S. Jones, Menlo Park, CA (US); Joseph Rimsa, Palo Alto, CA (US)

(73) Assignee: TauTona Group Research and Development Company, L.L.C., Menlo Park, CA (US)

( * ) Notice: Subject to any disclaimer, the term of this patent is extended or adjusted under 35 U.S.C. 154(b) by 677 days.

(21) Appl. No.: 13/606,517

(22) Filed: Sep. 7, 2012

(65) Prior Publication Data

US 2013/0116782 A1 May 9, 2013

Related U.S. Application Data

(60) Provisional application No. 61/532,734, filed on Sep. 9, 2011.

(51) Int. Cl.
*A61F 2/12* (2006.01)
*A61B 19/00* (2006.01)

(52) U.S. Cl.
CPC .. *A61F 2/12* (2013.01); *A61B 19/24* (2013.01)

(58) Field of Classification Search
CPC ....................................................... A61B 19/24
USPC ........................................................... 425/2
See application file for complete search history.

(56) References Cited

U.S. PATENT DOCUMENTS

| 1,922,947 | A | | 8/1933 | Grotte |
| 4,778,465 | A | | 10/1988 | Wilkins |
| 4,790,309 | A | * | 12/1988 | Becker .............................. 606/1 |
| 4,870,977 | A | | 10/1989 | Imonti |
| 5,171,321 | A | | 12/1992 | Davis |
| 5,520,613 | A | | 5/1996 | Copelan |
| 5,662,583 | A | * | 9/1997 | Khouri ............................ 600/38 |
| 5,871,456 | A | | 2/1999 | Armstrong et al. |
| 6,010,466 | A | | 1/2000 | McGeorge |
| 6,042,537 | A | | 3/2000 | Kaiser |
| 6,071,309 | A | | 6/2000 | Knowlton |
| 6,500,112 | B1 | | 12/2002 | Khouri |

(Continued)

FOREIGN PATENT DOCUMENTS

| DE | 10033891 | 1/2002 |
| GB | 635433 | 4/1950 |

*Primary Examiner* — Yogendra Gupta
*Assistant Examiner* — Kimberly A Stewart
(74) *Attorney, Agent, or Firm* — Levine Bagade Han LLP (57) ABSTRACT

Apparatus and methods for nipple and breast formation are described where devices precondition or expand a target nipple tissue to reduce the pressure exerted by the skin on an eventual implant. Generally, the apparatus comprises a mold having a contact surface which is curved in conformance with a breast upon which the mold is positionable, the contact surface having an adhesive for securement upon the breast, and the mold defining a cavity along the contact surface which conforms to a size of a nipple to be formed upon the breast and where the cavity further comprises the adhesive for securement to the nipple. A breast enlargement device comprises a cup larger than the target breast and further defines an inner surface which adheres to the breast when contacted.

12 Claims, 6 Drawing Sheets

(56) References Cited

U.S. PATENT DOCUMENTS

| | | |
|---|---|---|
| 6,641,527 B2 | 11/2003 | Khouri |
| 7,648,467 B2 | 1/2010 | Wang et al. |
| 7,938,122 B2 | 5/2011 | Clark |
| 2003/0073930 A1 | 4/2003 | Morrissey et al. |
| 2005/0267386 A1* | 12/2005 | Copelan ......................... 601/14 |
| 2006/0106329 A1 | 5/2006 | Hammer et al. |
| 2008/0071370 A1 | 3/2008 | Vinas |
| 2008/0188787 A1 | 8/2008 | Clark |
| 2011/0054374 A1 | 3/2011 | Hyde-Edwards et al. |
| 2011/0184355 A1 | 7/2011 | Kurz et al. |

* cited by examiner

APPARATUS AND METHODS FOR NIPPLE FORMATION VIA COLLAPSIBLE DEVICES

CROSS-REFERENCE TO RELATED APPLICATIONS IONS

This application is a non-provisional of and claims the benefit of priority to U.S. Provisional Patent Application No. 61/532,734 filed Sep. 9, 2011, the content of which is incorporated herein by reference in its entirety.

FIELD OF THE INVENTION

The present invention relates generally to medical devices and methods used for nipple reconstruction. More particularly, the present invention relates to apparatus and methods for nipple reconstruction utilizing devices which are mechanically simple to utilize.

BACKGROUND OF THE INVENTION

In a majority of mastectomies, the nipple is not preserved. While breast implants are an option for women who would like to have their breasts reconstructed, nipple reconstruction is still a challenging problem which lacks good options. Currently, surgeons do their best to recreate a nipple, e.g., by cinching skin together and/or implanting the nipple area with some filler or material such as a biomaterial or some allograft. The inherent challenge is that the skin, which is taut, tends to push any additive material into the body making the nipple appear flat.

Although techniques for nipple-saving mastectomies exist, in most cases, the nipple and areola tissue are removed. There is no established gold standard procedure for nipple reconstruction, however, with all techniques permanence of nipple projection is inconsistent or problematic, and therein is an unmet clinical need.

An example of a commercially available product that helps enlarge or precondition breasts prior to fat grafting is the BRAVA® (Brava, LLC Miami, Fla.) which is typically worn at night by the user while sleeping.

However, the user is generally required to wear the device for a minimum of 10 hours per day for 10 to 14 consecutive weeks. This is usually very challenging given that a small pump must be worn in addition to the molds and a sports bra-like garment. Patient compliance is often a big challenge with BRAVA, and further it is not intended for or capable of nipple expansion.

SUMMARY OF THE INVENTION

A nipple forming apparatus which may precondition, expand or maintain target nipple tissue may be utilized to reduce the pressure exerted by the skin on an implant. Generally, the apparatus may comprise a mold having a contact surface which is curved in conformance with a breast upon which the mold is positionable, the contact surface comprising an adhesive for securement upon the breast, and the mold defining a cavity along the contact surface which conforms to a size of a nipple to be formed or that has been formed by an implant upon the breast and where the cavity further comprises the adhesive for securement to the nipple.

In use, a first mold having a contact surface which is curved may be adhered upon a breast such that the mold conforms to a surface of the breast. The mold may further define a first cavity along the contact surface which will precondition or expand the skin on the breast that will eventually be formed into a nipple. This mold is adhered to a portion of the breast and is maintained upon the breast for a first period of time. The mold is then removed from the breast and a second mold having a contact surface is adhered upon the breast where the second mold defines a second cavity which is equal to or larger than the first cavity. The second mold is maintained upon the breast for a second period of time such that a size of the nipple is maintained when the second mold is removed from the breast. This process is repeated with subsequent molds as necessary to achieve the desired preconditioned or expansion.

When desired result is achieved, the mold can be removed and an implant placed in the newly formed nipple envelop. It may be desirable to adhere an appropriately sized mold after placing the implant within the nipple, which may hold the nipple in the desired conformation while some degree of settling takes place.

BRIEF DESCRIPTION OF THE DRAWINGS

FIGS. 1, 2 and 3 are different views of the mold.

DETAILED DESCRIPTION OF THE INVENTION

Generally, the cause of nipple flattening is multi-factorial and includes inadequate subcutaneous fat internal pressure, external pressure, poor flap design, delayed healing, and tissue memory. Poor flap design, inadequate subcutaneous fat and delayed healing are more related to surgical technique. Permanent implants like ARTECOLL® (Artes Medical, Inc., San Diego, Calif.) or absorbable allografts like ALLODERM® (LifeCell Corp., Branchburg N.J.) have been used to address the issues of internal and external pressure as well as tissue memory however these projections reduce over time. The devices and methods described herein address the internal and external pressures and tissue memory thereby making implants as described in U.S. Pat. No. 4,778,465, Surgically implantable areola and nipple prosthesis, more likely to persist.

Generally, the devices described herein precondition, expand or maintain the target nipple tissue (which is homogenous post-mastectomy) which reduces the pressure exerted on an implant by the skin. This can be done multiple ways where one variation may utilize an external mold that is adhered to the nipple target skin to create laxity in the skin prior to the implantation of a filler, whether fat or a biomaterial. Once the nipple skin is expanded, an implant such as ALLODERM® or a cylinder of hyaluronic acid threads or a chitosan sponge, for example, is surgically implanted. By creating a space, the forces acting on the nipple implant to drive it into the body may be minimized or rendered non-existent. In another variation designed to maintain nipple tissue, after implanting a filler to create the nipple shape, an external mold is adhered to the newly created nipple projection to reduce or eliminate the external pressure exerted by the skin on the implant while the skin remodels, allowing the nipple projection to be maintained.

Figure 1:
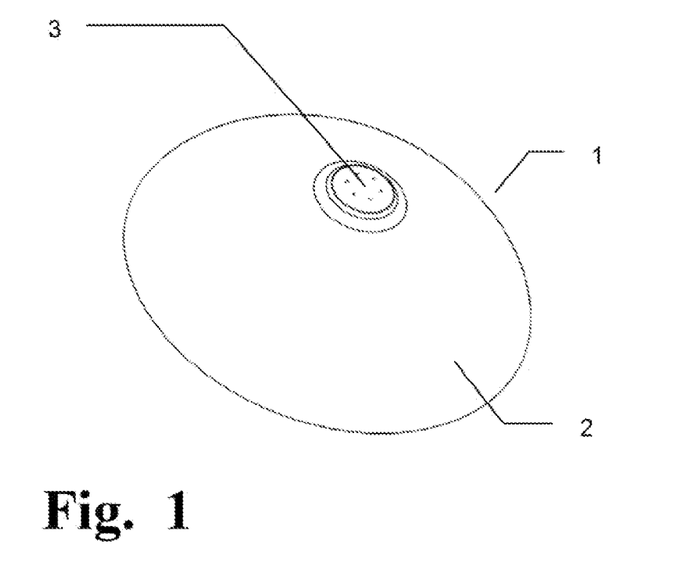
FIG. 1 is a near isometric view of the top.
Figure 2:
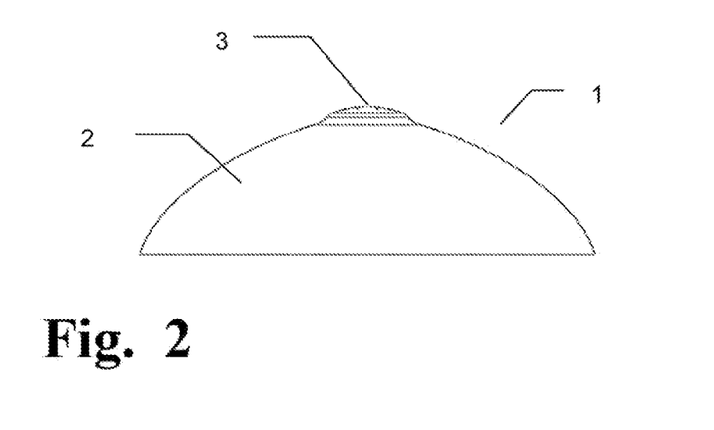
FIG. 2 is a side view and FIG. 3 is a near isometric view of the bottom.
Figure 3:
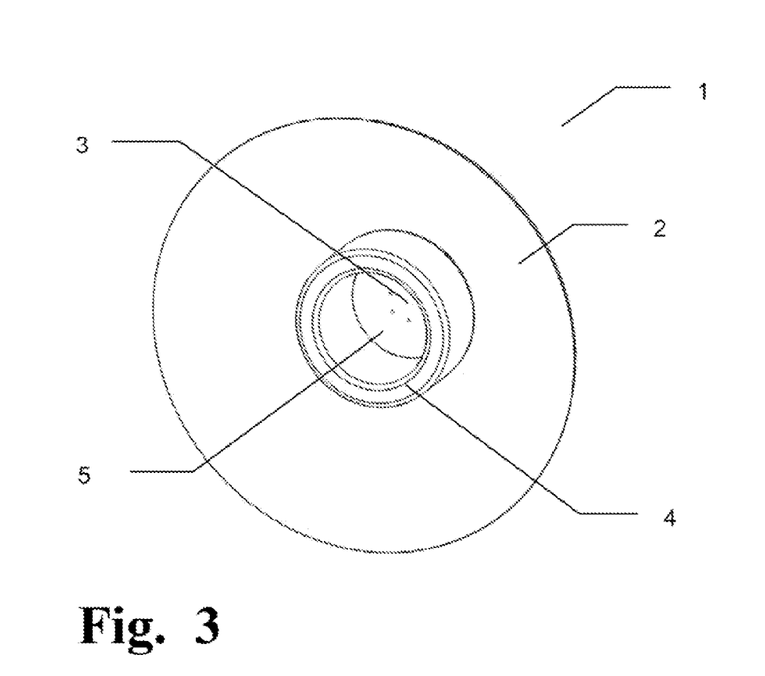

FIGS. 1-3 show one variation of a first nipple forming mold 1 that may be adhered to a post-mastectomy breast which has had its nipple surgically removed. The mold 1 may comprise an elastomeric material which has a formed external shaped which is configured to match the contour of the underlying breast. The contact surface of the mold 1 which contacts the breast may have an adhesive layered upon the surface to adhere the mold 1 directly to the skin of the breast. The mold 1 may also define a pocket into which the nipple, or soon-to-be nipple skin, is to be adhered directly via an adhesive surface. The nipple skin may be undersized to the nipple mold if the device is used to expand the nipple tissue. If the device is used to maintain the nipple tissue, a nipple mold which is equally sized to the nipple may be used.

Figure 4:
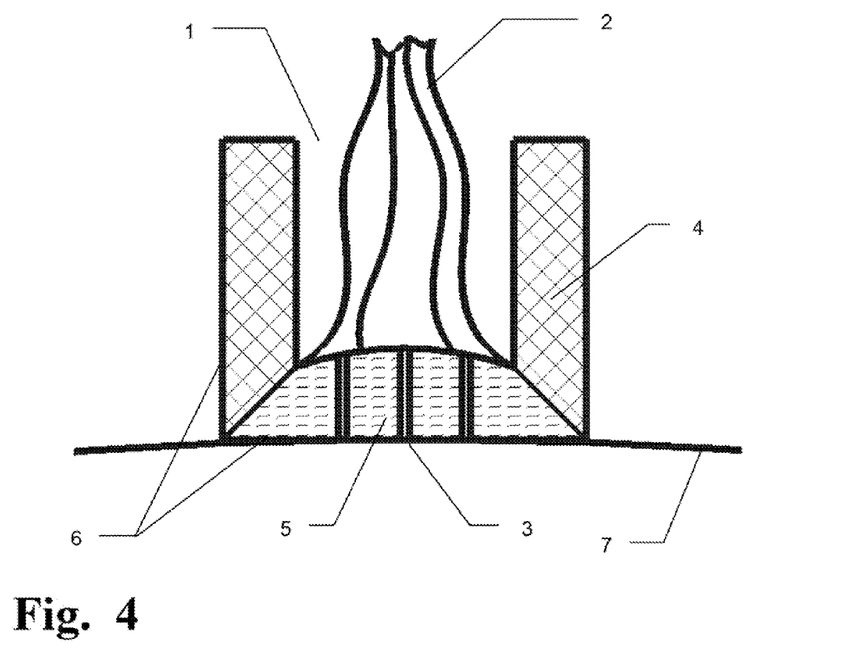
FIG. 4 shows a variation of the mold having at least two regions of differing stiffness, in an inverted position, with the adhesive surface placed on breast tissue.

Pressing the mold 1 on the top of the dome will invert the mold 1 to the configuration seen in FIG. 4. Inverting the mold 1 folds the mold skirt 2 into the center and out of the way and makes positioning and adhering the adhesive surface 6 of the optionally higher stiffness/durometer mold section 5 to the target area on the breast tissue 7. The mold 1 may be made from an elastomeric material having a first stiffness/durometer of Shore A 30-70, more specifically Shore A 50. The receiving cavity may have a second stiffness/durometer of Shore A 40-80, more specifically Shore A 58, which is higher than the first stiffness/durometer.

Figure 5:
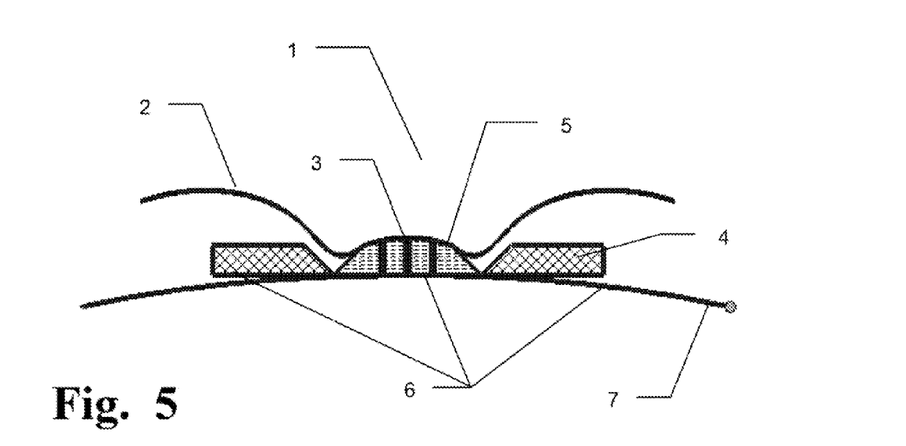
FIG. 5 shows a variation of the mold having at least two regions of differing stiffness, in a partially inverted position, with the all the adhesive surfaces placed, on the breast and deploying to recruit skin into the mold.
Figure 6:
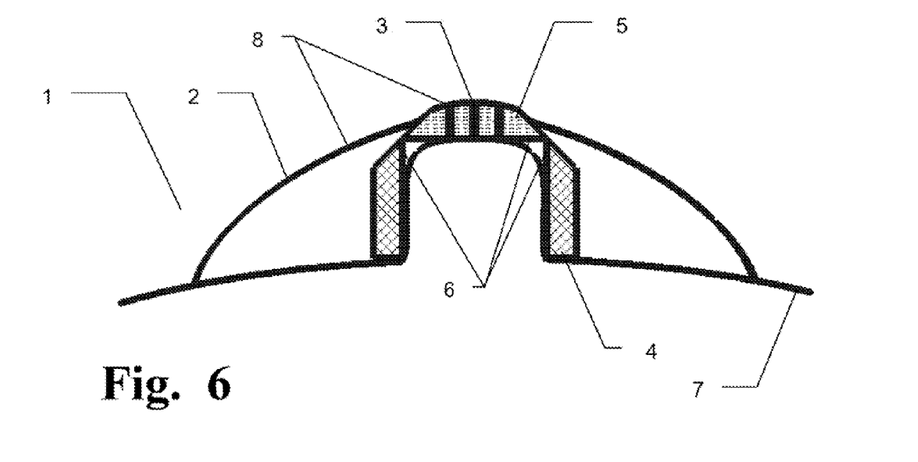
FIG. 6 shows a variation of the mold having at least two regions of differing stiffness, in a deployed position, with breast tissue recruited into the mold and the protective, low friction skirt deployed.

Once adhered to the target area on the breast tissue 7, the mold reversion process is initiated as shown in FIG. 5. As the sides of the nipple mold 4 revert, the adhesive surface 6 adheres to tissue adjacent to the target area on the breast tissue. When reversion is complete and the nipple mold 4 has returned to the relaxed state, the sides of the nipple mold 4 are shown to have adhered to the breast tissue 7 and recruited the adhered breast tissue 7 into the mold 1 as shown in FIG. 6. The mold skirt 2 fully deploys to both protect and smooth the appearance of the mold 1. The low friction material/covering/coating 8 on the mold skirt 2 ensures any local rubbing from clothes or other fabric minimizes any transmitted stress or strain on the mold 1.

Figure 7:
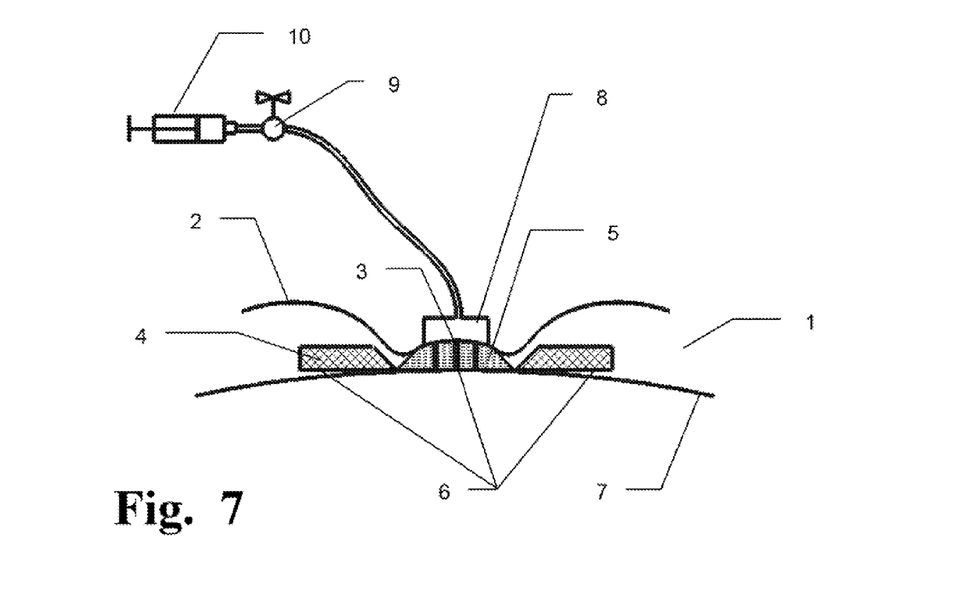
FIG. 7 shows a vacuum source assisting to adhere the variation of the mold having at least two regions of differing stiffness, in a partially inverted position, with all the adhesive surfaces placed on the breast, deploying to recruit skin into the mold.

In yet another variation, another embodiment may comprise stretching the breast tissue to form the nipple with the assistance of a suction or vacuum force. As shown in the partial cross-sectional side view of FIG. 7, the molding device may comprise a contoured mold, as previously described, but also including one or more openings 3 through the device in communication with the nipple molding cavity.

Figure 8:
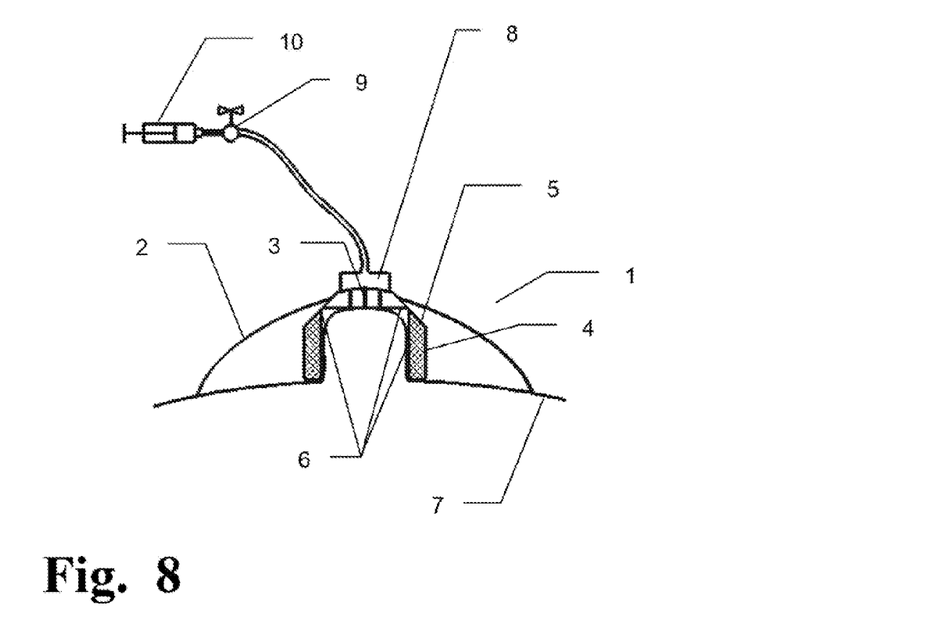
FIG. 8 shows a vacuum source assisting to adhere and recruit skin into the variation of the mold having at least two regions of differing stiffness, in a deployed position, with breast tissue recruited into the mold and the protective, low friction skirt deployed.

When the device is released and allowed to revert back towards its relaxed configuration as seen in FIG. 8, the adhered breast tissue may be pulled to create skin laxity within the nipple molding cavity. A vacuum or suction force 8 may be optionally applied through the openings via a vacuum pump 9, 10 to further draw the skin into the nipple molding cavity to ensure adherence of the skin to the mold. Once the tissue has been adhered, the vacuum may be desirably removed or left on until the next mold is required.

Aside from the openings 3 for allowing fluid communication with a vacuum source, the openings 3 may also serve to allow for any sweat or fluid from the adhered skin to evaporate through the openings 3. Additionally and/or alternatively, the material forming the sides or walls of the nipple mold 4 may also define one or more openings therethrough to allow for sweat or fluids to evaporate from the underlying skin. Aside from the one or more openings, the material and/or adhesive may be permeable to fluid.

Clinical experience has shown that forming the nipple must be done gradually. Attempting to recruit skin too quickly creates high stress/strain concentrations in the skin that can lead to blisters, tears, infection and/or scarring. This can delay the process and complicate further nipple formation efforts. To minimize the risk, one or more molds may be utilized in progression where each subsequent mold may define a nipple mold which is progressively larger than the previous mold to subsequently stretch the nipple into a progressively larger size.

Figure 9:
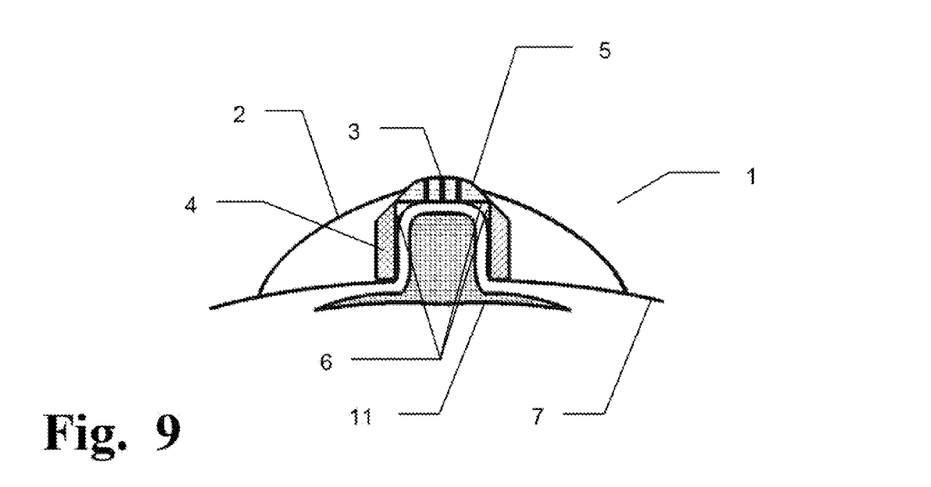
FIG. 9 shows an implant placed under a formed nipple within a mold.
Figure 10:
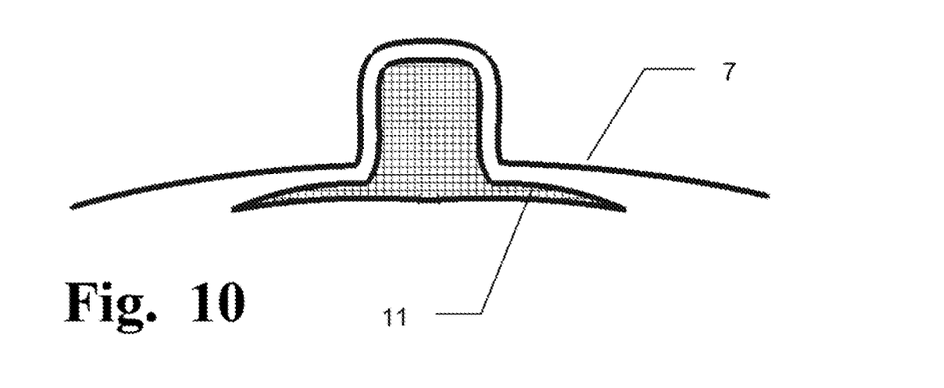
FIG. 10 shows an implant placed under a formed nipple without a mold.

Once the progression of one or more is completed and the patient has reached the required nipple size, expansion may be stopped and an implant 11 material or filler such as fat or a biomaterial may be inserted to permanently form the nipple as shown in FIG. 10. Optionally, and after the implant 11, a mold ma be reapplied to the newly formed nipple with implant 11 as shown in FIG. 9 to allow time for the tissue and implant 11 to equilibrate.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A nipple forming apparatus, comprising:
a mold having a contact surface which is curvable in conformance with a breast upon which the mold is positionable, wherein the contact surface comprises an adhesive for securement upon the breast, the mold having a first collapsed configuration for adhering to a region of the breast and a second molding configuration which defines a receiving cavity for drawing the adhered region of the breast away from a remainder of the breast; and
a mold skirt which is attached to a portion of the mold and is reconfigurable between a first extended configuration where the mold in its first collapsed configuration is positionable against the region of the breast and a second supporting configuration where the mold skirt forms a smoothed surface relative to the mold in its second molding configuration.

2. The apparatus of claim 1 wherein the mold is invertible.

3. The apparatus of claim 1 wherein the mold is hollow.

4. The apparatus of claim 1 wherein the mold is made from an elastomeric material having a first stiffness/durometer of Shore A 30-70 and the receiving cavity has a second stiffness/durometer of Shore 40-80 which is higher than the first stiffness/durometer.

5. The apparatus of claim 1 wherein the elastomer is biocompatible.

6. The apparatus of claim 1 wherein the cavity defines one or more openings therethrough.

7. The apparatus of claim 1 wherein the mold has a feature indicating where the nipple will form when applied to the region of the breast.

8. The apparatus of claim 5 further comprising a vacuum pump in fluid communication with the one or more openings.

9. The apparatus of claim 1 further comprising a distensible ring which has a first surface adherable to the breast and which further defines an opening through which the nipple may be positioned.

10. The apparatus of claim 1 wherein the mold skirt has a low friction surface.

11. The apparatus of claim 1 wherein the mold is invertible and a portion of the cavity is adhered to the region of the breast while inverted, thereupon the mold is reverted back to its nominal configuration, which recruits and stretches the region of the breast, and the remainder of the cavity is adhered to the region of the breast, securing the recruited and stretched region of the breast in place within the receiving cavity.

12. The apparatus of claim 1 wherein the mold or series of molds defines a cavity along the contact surface which conforms to a size of a nipple to be formed upon the breast and where the cavity further comprises the adhesive for securement to the nipple.

* * * * *